United States Patent [19]

Ross et al.

[11] Patent Number: 5,310,927

[45] Date of Patent: May 10, 1994

[54] BENZOFURAN DERIVATIVES

[75] Inventors: Barry C. Ross; David Middlemiss; David I. C. Scopes; Torquil I. M. Jack; Kevin S. Cardwell; Michael D. Dowle; Duncan B. Judd, all of Ware, Great Britain

[73] Assignee: Glaxo Group Limited, London, England

[21] Appl. No.: 883,164

[22] Filed: May 15, 1992

[30] Foreign Application Priority Data

May 16, 1991 [GB] United Kingdom ............ 9110625.2

[51] Int. Cl.$^5$ ............... C07D 407/12; C07D 407.14; A61K 31/41; A61K 31/415
[52] U.S. Cl. ........................ 548/251; 548/117; 548/118; 548/266.6; 548/315.4
[58] Field of Search ............ 514/382, 397, 383, 93; 548/251, 266.6, 315.4, 117, 118

[56] References Cited

U.S. PATENT DOCUMENTS

| | | | |
|---|---|---|---|
| 4,229,460 | 10/1980 | Heeves et al. | 514/382 |
| 4,503,236 | 3/1985 | Unangst | 548/252 |
| 4,526,896 | 7/1985 | Scherrer | 548/252 |
| 4,703,053 | 10/1987 | Connor et al. | 548/252 |

FOREIGN PATENT DOCUMENTS

| | | |
|---|---|---|
| 0253310 | 1/1988 | European Pat. Off. . |
| 0384450 | 8/1990 | European Pat. Off. ............ 548/251 |
| 0434249 | 6/1991 | European Pat. Off. . |
| WO91/00281 | 1/1991 | PCT Int'l Appl. . |

OTHER PUBLICATIONS

Timmermans et al., TIPS, 12, Feb. 1991, pp. 55–62.

Primary Examiner—David B. Springer
Attorney, Agent, or Firm—Bacon & Thomas

[57] ABSTRACT

The invention provides compounds of formula (I):

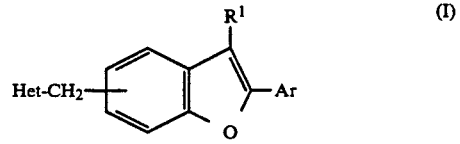

or a physiologically acceptable salt, solvate or metabolically labile ester thereof wherein $R^1$ represents a hydrogen atom or a halogen atom or a group selected from $C_{1-6}$alkyl, $C_{2-6}$alkenyl, fluoro$C_{1-6}$alkyl, $C_{1-6}$alkoxy, —CHO, —$CO_2H$ or —$COR^2$;

Ar represents the group

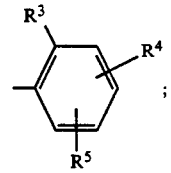

Het represents an N-linked imidazolyl group optionally substituted by one, two or three substituents.

The compounds may be used in the treatment or prophylaxis of hypertension and diseases associated with cognitive disorders.

16 Claims, No Drawings

BENZOFURAN DERIVATIVES

This invention relates to benzofuran derivatives, processes for their preparation and pharmaceutical compositions containing them. According to a first aspect of the invention we provide a compound of the general formula (I):

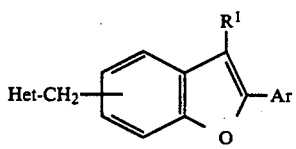

or a physiologically acceptable salt, solvate (e.g. hydrate) or metabolically labile ester thereof in which $R^1$ represents a hydrogen atom or a halogen atom or a group selected from $C_{1-6}$alkyl, $C_{2-6}$alkenyl, fluoro$C_{1-6}$alkyl, $C_{1-6}$alkoxy —CHO, —CO$_2$H or —COR$^2$;

Ar represents the group

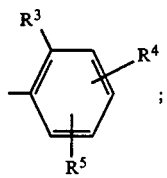

$R^2$ represents a group selected from $C_{1-6}$alkyl, $C_{2-6}$alkenyl, $C_{1-6}$alkoxy or the group —NR$^{10}$R$^{11}$;

$R^3$ represents a group selected from —SO$_3$R$^{15}$, —PO(OR$^{15}$)$_2$, —PO(OR$^{16}$)R$^{16}$, —SO$_2$NHR$^{16}$, —CONHOR$^{16}$, —CONHNHSO$_2$CF$_3$, —SO$_2$NH—heteroaryl, —CH$_2$SO$_2$NH-heteroaryl, —SO$_2$NHCOR$^{17}$, —CH$_2$SO$_2$NHCOR$^{17}$, —CONHSO$_2$R$^{17}$, —CH$_2$CONHSO$_2$R$^{17}$, —NHSO$_2$NHCOR$^{17}$, —NHCONHSO$_2$R$^{17}$. —SO$_2$NHCONHR$^{17}$, —CONHSO$_2$NHR$^{17}$,

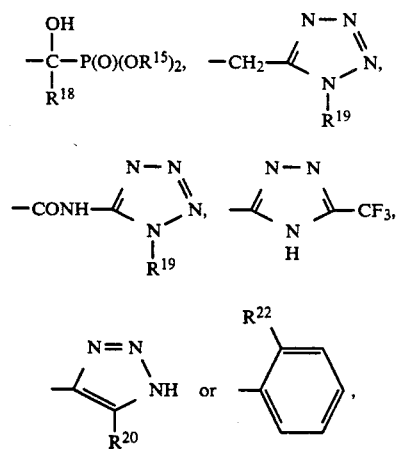

wherein 'heteroaryl' represents a 5 or 6 membered aromatic ring containing from 1 to 3 heteroatoms selected from the group consisting of N, O or S, said aromatic ring being optionally substituted by 1 or 2 substituents selected from a halogen atom or a group selected from hydroxy, —SH, $C_{1-4}$alkyl, $C_{1-4}$alkoxy, —CF$_3$, —NO$_2$, —CO$_2$H, $C_{1-5}$acyloxy, —NH$_2$, $C_{1-4}$alkylamino or di$C_{1-4}$alkylamino; $R^4$ and R 5 which may be the same or different each independently represent a hydrogen atom or a halogen atom or a $C_{1-6}$alkyl group;

Het represents an N-linked imidazolyl group optionally substituted at the 2-position by a $C_{1-6}$alkyl, $C_{2-6}$alkenyl, $C_{1-6}$alkylthio, $C_{1-6}$alkoxy, $C_{3-7}$cycloalkyl or $C_{3-7}$cycloalkyl$C_{1-4}$alkyl group, the imidazolyl group optionally being substituted at the 4-and 5-positions by one or two further substituents selected from a halogen atom or a group selected from cyano, nitro, $C_{1-6}$alkyl, $C_{2-6}$alkenyl, fluoro$C_{1-6}$alkyl, $C_{3-7}$cycloalkyl, $C_{3-7}$cycloalkyl$C_{1-4}$alkyl, —(CH$_2$)$_m$R$^6$, —(CH$_2$)$_n$COR$^7$ or —(CH$_2$)$_p$NR$^8$COR$^9$;

$R^6$ represents a hydroxy or $C_{1-6}$alkoxy group;

$R^7$ represents a hydrogen atom or a group selected from hydroxy, $C_{1-6}$alkyl, $C_{1-6}$alkoxy, phenyl, phenoxy or the group —NR$^{10}$R$^{11}$;

$R^8$ represents a hydrogen atom or a $C_{1-6}$alkyl group;

$R^9$ represents a hydrogen atom or a group selected from $C_{1-6}$alkyl, $C_{1-6}$alkoxy, phenyl, phenoxy or the group —NR$^{10}$R$^{11}$;

$R^{10}$ and $R^{11}$, which may be the same or different, each independently represent a hydrogen atom or a $C_{1-4}$alkyl group, or —NR$^{10}$R$^{11}$ forms a saturated heterocyclic ring which has 5 or 6 ring members and may optionally contain in the ring one oxygen atom;

$R^{15}$ represents a hydrogen atom or the group —CH(R$^{16}$)OC(O)R$^{21}$.

$R^{16}$ represents a hydrogen atom or a group selected from $C_{1-6}$alkyl, phenyl or benzyl;

$R^{17}$ represents a group selected from aryl, heteroaryl (as defined above), $C_{3-7}$cycloalkyl, perfluoro$C_{1-4}$alkyl or $C_{1-4}$alkyl optionally substituted by a halogen atom or a group selected from hydroxy, —SH, $C_{1-4}$alkyl, $C_{1-4}$alkoxy, $C_{1-4}$alkylthio, —CF$_3$, —NO$_2$, —CO$_2$H, —C$_{1-5}$acyloxy, —NH$_2$, $C_{1-4}$alkylamino, di$C_{1-4}$alkylamino, —PO$_3$H or —PO(OH)$C_{1-4}$alkoxy, wherein aryl, represents a phenyl or naphthalenyl group optionally substituted by 1 or 2 substituents selected from a halogen atom or a group selected from $C_{1-4}$alkyl, $C_{1-4}$alkoxy, —NO$_2$, —CF$_3$, $C_{1-4}$alkylthio, hydroxy or —NH$_2$;

$R^{18}$ represents a hydrogen atom or a group selected from $C_{1-6}$alkyl, phenyl or benzyl;

$R^{19}$ represents a hydrogen atom or a group selected from $C_{1-6}$alkyl, $C_{2-4}$alkenyl or $C_{1-4}$alkoxy$C_{1-4}$alkyl;

$R^{20}$ represents a group selected from —CN, —NO$_2$ or —CO$_2$R$^{16}$;

$R^{21}$ represents a group selected from $C_{1-6}$alkyl, aryl (as defined above) or —CH$_2$-aryl (as defined above);

$R^{22}$ represents a group selected from —CO$_2$R$^{16}$, —SO$_3$R$^{15}$, —NHSO$_2$CF$_3$, —PO(OR$^{15}$)$_2$, —SO$_2$NHR$^{18}$ or a C-linked tetrazolyl group;

m represents an integer from 1 to 4, preferably 1 or 2, especially 1;

n represents an integer from 0 to 4, preferably 0, 1 or 2, especially 0 or 1; and p represents an integer from 1 to 4, preferably 1 or 2.

Where the compound of general formula (I) is optically active said formula (I) is intended to cover all enantiomers, (I). diastereoisomers and mixtures thereof including racemates. Where a compound of the present invention contains one or more double bonds, these may exist in the cis or trans configuration. Furthermore, where such geometric isomers exist, formula (I) is intended to cover mixtures thereof.

The invention also includes within its scope the solvates, especially the hydrates of compounds of general formula Within the above definition the term 'alkyl', 'alkoxy', 'alkylthio' or 'acyl' is a group or part of a group means that the group is straight or branched. Examples of suitable alkyl groups include methyl, ethyl, propyl or butyl groups. The term 'alkenyl' as a group or part of a group means that the group is straight or branched and contains at least one carbon-carbon double bond. The term 'cycloalkyl' as a group or part of a group may be, for example, a cyclopropyl, cyclobutyl, cyclopentyl or cyclohexyl group.

The term 'halogen' means a fluorine, chlorine, bromine or iodine atom.

The term 'fluoroC$_{1-6}$alkyl' means a C$_{1-6}$alkyl group in which one or more hydrogen atoms have been replaced by a fluorine atom, for example, —CH$_2$CF$_3$. Particularly preferred are 'perfluoroC$_{1-3}$alkyl' groups meaning a fully fluorinated C$_{1-3}$alkyl group, i.e. trifluoromethyl, pentafluoroethyl, heptafluoropropyl or heptafluoroisopropyl.

Within the above definition when —NR$^{10}$R$^{11}$ represents a saturated heterocyclic ring, this contains 5 or 6 ring members, one of which may be an oxygen atom. Suitable heterocyclic groups are a pyrrolidino, piperidino or morpholino group.

A preferred class of compounds of general formula (I) is that wherein the group Het is substituted at the 2-position by a hydrogen atom or a C$_{1-5}$alkyl, especially a C$_{2-5}$alkyl group or a C$_{3-5}$alkenyl group. Particularly preferred are those compounds wherein the 2-position substituent is an ethyl, n-propyl or n-butyl group, especially an ethyl group. Conveniently, the C$_{3-5}$alkenyl group may be a but-1-enyl group.

Another preferred class of compounds of general formula (I) is that wherein the group Het is optionally substituted by one or two further substituents selected from a halogen atom (especially a chlorine atom) or a group selected from C$_{1-6}$alkyl, —(CH$_2$)$_m$R$^6$ or —(CH$_2$)$_n$COR$^7$. In particular, R$^6$ represents a hydroxy or C$_{1-6}$alkoxy group, and preferably a hydroxy, methoxy, ethoxy, propoxy or butoxy group, and especially a hydroxy or methoxy group. R$^7$, in particular, represents a hydrogen atom or a hydroxy, C$_{1-6}$alkoxy or —NR$^{10}$R$^{11}$ group (especially wherein R$^{10}$ and R$^{11}$ each independently represent a hydrogen atom or a C$_{1-4}$alkyl group), and preferably a hydrogen atom or a hydroxy, methoxy, ethoxy, propoxy or butoxy group, and especially a hydrogen atom or a hydroxy or methoxy group, and m is 1 or 2 and n is 0, 1 or 2.

A further preferred class of compound of general formula (I) is that wherein the group Het is substituted by a further substituent selected from C$_{3-5}$cycloalkyl or C$_{3-5}$cycloalkylC$_{1-2}$alkyl, especially a cyclopropyl, cyclobutyl or cyclopropylmethyl group.

In particularly preferred embodiments of the present invention, the substituents are chosen from a chlorine atom and a group selected from —CH$_2$OH, —CHO, —CH$_2$OCH$_3$, —CO$_2$H, —CO$_2$CH$_3$, —CO$_2$CH$_2$CH$_3$, —CONH$_2$ and —CONHCH$_3$.

A yet further preferred class of compounds of general formula (I) is that wherein R$^1$ represents a hydrogen atom or a halogen atom or a group selected from C$_{1-6}$alkyl, C$_{1-6}$alkoxy or fluoroC$_{1-6}$alkyl, and in particular a hydrogen atom or halogen atom or a C$_{1-3}$alkyl group.

Especially preferred are compounds wherein R$^1$ is a bromine atom.

Conveniently, in the compounds of general formula (I), the group Het—CH$_2$— is attached at the 5- or 6-position on the benzofuran ring, and especially the 5-position.

Another preferred class of compounds of general formula (I) is that wherein R$^3$ represents the group —CONHSO$_2$R$^{17}$ (especially where R$^{17}$ represents a phenyl group) or the group

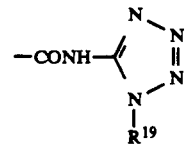

especially where R$^{19}$ represents a hydrogen atom.

Also conveniently, in the compounds of general formula (I), R$^4$ and R$^5$ may each independently represent a hydrogen atom or a halogen atom. In particular R$^4$ and R$^5$ each represent hydrogen atoms.

Particularly preferred compounds of the invention include:

1-[[3-bromo-2-[2-[[(phenylsulphonyl)amino]carbonyl]-phenyl]-5-benzofuranyl]methyl]-2-ethyl-4-methyl-1H-imidazole-5-carboxamide;

1-[[3-bromo-2-[2-[[(phenylsulphonyl)amino]carbonyl]-phenyl]-5-benzofuranyl]methyl]-2-ethyl-N,4-dimethyl-1H-imidazole-5-carboxamide;

1-[[3-bromo-2-[2-[[(phenylsulphonyl)amino]carbonyl]-phenyl)-5-benzofuranyl]methyl]-N,2-diethyl-4-methyl-1H-imidazole-5-carboxamide;

1-[[3-bromo-2-[2-[[(phenylsulphonyl)amino]carbonyl]-phenyl]-5-benzofuranyl]methyl]-4-chloro-2-ethyl-1H-imidazole-5-carboxamide;

1-[[3-bromo-2-[2-[[(phenylsulphonyl)amino]carbonyl]-phenyl]-5-benzofuranyl]methyl]-4-chloro-2-ethyl-N-methyl-1H-imidazole-5-carboxamide;

1-[[3-bromo-2-[2-[[(phenylsulphonyl)amino]carbonyl]-phenyl]-5-benzofuranyl]methyl]-4-chloro-N,2-diethyl-1H-imidazole-5-carboxamide;

1-[[3-bromo-2-[2-[[(phenylsulphonyl)amino]carbonyl]-phenyl]-5-benzofuranyl]methyl]-4-methyl-2-propyl-1H-imidazole-5-carboxamide;

1-[[3-bromo-2-[2-[[(phenylsulphonyl)amino]carbonyl]-phenyl]-5-benzofuranyl]methyl]-N,4-dimethyl-2-propyl-1H-imidazole-5-carboxamide;

1-[[3-bromo-2-[2-[[(phenylsulphonyl)amino]carbonyl]-phenyl]-5-benzofuranyl]methyl]-N-ethyl-4-methyl-2-propyl-1H-imidazole-5-carboxamide;

1-[[3-bromo-2-[2-[[(phenylsulphonyl)amino]carbonyl]-phenyl]-5-benzofuranyl]methyl]-4-chloro-2-propyl-1H-imidazole-5-carboxamide;

1-[[3-bromo-2-[2-[[(phenylsulphonyl)amino]carbonyl]-phenyl]-5-benzofuranyl]methyl]-4-chloro-N-methyl-2-propyl-1H-imidazole-5-carboxamide;

1-[[3-bromo-2-[2-[[(phenylsulphonyl)amino]carbonyl]-phenyl]-5-benzofuranyl]methyl]-4-chloro-N-ethyl-2-propyl-1H-imidazole-5-carboxamide;

1-[[3-bromo-2-[2-[[(1H-tetrazol-5-yl)amino]carbonyl]-phenyl]-5-benzofuranyl]methyl]-2-ethyl-4-methyl-1H-imidazole-5-carboxamide;

1-[[3-bromo-2-[2-[[(1H-tetrazol-5-yl)amino]carbonyl]-phenyl]-5-benzofuranyl]methyl]-2-ethyl-N,4-dimethyl-1H-imidazole-5-carboxamide;

1-[[3-bromo-2-[2-[[(1H-tetrazol-5-yl)amino]carbonyl]-phenyl]-5-benzofuranyl]methyl]-N,2-diethyl-4-methyl-1H-imidazole-5-carboxamide;
1-[[3-bromo-2-[2-[[(1H-tetrazol-5-yl)amino]carbonyl]-phenyl]-5-benzofuranyl]methyl]-4-chloro-2-ethyl-1H-imidazole-5-carboxamide;
1-[[3-bromo-2-[2-[[(1H-tetrazol-5-yl)amino)carbonyl]-phenyl]-5-benzofuranyl]methyl]-4-chloro-2-ethyl-N-methyl-1H-imidazole-5-carboxamide;
1-[[3-bromo-2-[2-[[(1H-tetrazol-5-yl)amino]carbonyl]-phenyl]-5-benzofuranyl]methyl]-4-chloro-N,2-diethyl-1H-imidazole-5-carboxamide;
1-[[3-bromo-2-[2-[[(1H-tetrazol-5-yl)amino]carbonyl]-phenyl]-5-benzofuranyl]methyl]-4-methyl-2-propyl-1H-imidazole-5-carboxamide;
1-[[3-bromo-2-[2-[[(1H-tetrazol-5-yl)amino]carbonyl]-phenyl]-5-benzofuranyl]methyl]-N,4-dimethyl-2-propyl-1H-imidazole-5-carboxamide;
1-[[3-bromo-2-[2-[[(1H-tetrazol-5-yl)amino]carbonyl]-phenyl]-5-benzofuranyl]methyl]-N-ethyl-4-methyl-2-propyl-1H-imidazole-5-carboxamide;
1-[[3-bromo-2-[2-[[(1H-tetrazol-5-yl)amino]carbonyl]-phenyl]-5-benzofuranyl]methyl]-4-chloro-2-propyl-1H-imidazole-5-carboxamide;
1-[[3-bromo-2-[2-[[(1H-tetrazol-5-yl)amino]carbonyl]-phenyl]-5-benzofuranyl]methyl]-4-chloro-N-methyl-2-propyl-1H-imidazole-5-carboxamide;
1-[[3-bromo-2-[2-[[(1H-tetrazol-5-yl)amino]carbonyl]-phenyl]-5-benzofuranyl]methyl]-4-chloro-N-ethyl-2-propyl-1H-imidazole-5-carboxamide;
and physiologically acceptable salts, solvates and metabolically labile esters thereof.

Further preferred compounds of the present invention include:
1-[[3-bromo-2-[2-[[(phenylsulphonyl)amino]carbonyl]-phenyl]-5-benzofuranyl]methyl]-4-cyclopropyl-2-ethyl-1H-imidazole-5-carboxylic acid;
1-[[3-bromo-2-[2-[[(phenylsulphonyl)amino]carbonyl]-phenyl]-5-benzofuranyl]methyl]-4-cyclopropyl-2-propyl-1H-imidazole-5-carboxylic acid;
1-[[3-bromo-2-[2-[[(phenylsulphonyl)amino]carbonyl]-phenyl)-5-benzofuranyl]methyl]-4-cyclopropyl-2-ethyl-1H-imidazole-5-carboxamide;
1-[[3-bromo-2-[i-[[(phenylsulphonyl)amino]carbonyl]-phenyl]-5-benzofuranyl]methyl]-4-cyclopropyl-2-propyl-1H-imidazole-5-carboxamide;
1-[[3-bromo-2-[2-[[(phenylsulphonyl)amino]carbonyl]-phenyl]-5-benzofuranyl]methyl]-4-cyclopropyl-2-ethyl-N-methyl-1H-imidazole-5-carboxamide;
1-[[3-bromo-2-[2-[[(phenylsulphonyl)amino]carbonyl]-phenyl)-5-benzofuranyl]methyl]-4-cyclopropyl-N-methyl-2-propyl-1H-imidazole-5-carboxamide;
1-[[3-bromo-2-[2-[[(phenylsulphonyl)amino]carbonyl]-phenyl)-5-benzofuranyl]methyl]-4-cyclopropyl-N,2-diethyl-1H-imidazole-5-carboxamide;
1-[[3-bromo-2-[2-[[(phenylsulphonyl)amino]carbonyl]-phenyl]-5-benzofuranyl]methyl]-4-cyclopropyl-N-ethyl-2-propyl-1H-imidazole-5-carboxamide;
and physiologically acceptable salts, solvates and metabolically labile esters thereof.

The physiologically acceptable acid addition salts of the compounds of formula (I) may be derived from inorganic or organic acids. Examples of such salts include hydrochlorides, hydrobromides, sulphates, phosphates, benzoates, methanesulphonates or trifluoroacetates.

The compounds may also form salts with suitable bases. Examples of such salts are alkali metal (e.g. sodium or potassium), alkaline earth metal (e.g. calcium or magnesium), ammonium and substituted ammonium (e.g. dimethylammonium, triethylammonium, 2-hydroxyethyldimethylammonium, piperazinium, N,N-dimethylpiperazinium, tetralkylammonium, piperidinium, ethylenediammonium and choline).

It will be appreciated that, for pharmaceutical use, the salts referred to above will be physiologically acceptable, but other salts may find use, for example, in the preparation of the compounds of formula (I) and the physiologically acceptable salts thereof.

It will be further appreciated that the compounds of general formula (I) may be chemically modified in the form of compounds which in vivo (for example, by enzymic attack) will provide the parent compounds of general formula (I). Such prodrugs may be, for example, physiologically acceptable metabolically labile ester derivatives. These may be formed by esterification, for example of any of the carboxylic acid groups in the parent compound of general formula (I), with prior protection of any other reactive groups present in the molecule. Examples of such esters include lower alkyl esters (e.g. methyl or ethyl esters), alkenyl esters (e.g. vinyl or allyl esters), alkynyl esters (e.g. ethynyl or propynyl esters), alkoxyalkyl esters, (e.g. methoxymethyl or 2-methoxyethyl esters), alkylthioalkyl esters (e.g. methylthiomethyl esters) haloalkyl esters (e.g. 2-iodoethyl or 2,2,2-trichloroethyl esters), alkanoyloxyalkyl esters (e.g. acetoxymethyl, 1-acetoxyethyl or pivaloyloxymethyl esters), alkoxycarbonyloxyalkyl esters (e.g. 1-ethoxycarbonyloxyethyl or 1-methoxycarbonyloxyethyl esters), aroyloxyalkyl esters (e.g. benzoyloxymethyl or 1-benzoyloxyethyl esters), substituted or unsubstituted aralkyl esters (e.g. benzyl or 4-amidobenzyl esters), substituted or unsubstituted aminoalkyl esters (e.g aminoethyl or 2-N,N-dimethylaminoethyl esters) or hydroxyalkyl esters (e.g. 2-hydroxyethyl or 2,3-dihydroxypropyl esters).

In addition to the above ester derivatives the present invention includes within its scope compounds of general formula (I) in the form of other physiologically acceptable equivalents, i.e. physiologically acceptable compounds which, like the metabolically labile esters, are converted in vivo into the parent compounds of general formula (I).

According to a second aspect of the present invention we provide a compound of general formula (I) or a physiologically acceptable salt, solvate or metabolically labile ester thereof for use in therapy.

In particular, the compounds of the present invention may be used in the treatment or prophylaxis of hypertension (for example, essential, malignant or resistant, caused by oral contraceptives, coarctation of the aorta or renal vascular disease) and pulmonary hypertension.

The compounds of the present invention may also be used in the treatment or prophylaxis of congestive heart failure, acute or chronic heart failure, aortic or cardiac insufficiency, post-myocardial infarction, renal insufficiency and renal failure (for example, as a result of diabetic nephropathy, glomerular nephritis, scleroderma or renal crisis), proteinuria, Bartter's syndrome, secondary hyperaldosteronism, Reynaud's syndrome, cerebrovascular insufficiency, peripheral vascular disease, diabetic retinopathy, atherogenesis and for the improvement of vascular compliance.

They are also potentially useful for the treatment of cognitive disorders such as dementia (e.g. Alzheimer's disease) and other CNS disorders, such as anxiety disorders, schizophrenia, depression and alcohol or drug (e.g. cocaine) dependency.

According to a further aspect of the present invention we provide a compound of general formula (I) or a physiologically acceptable salt, solvate or metabolically labile ester thereof for use in the treatment of the aforementioned diseases, especially hypertension.

According to another aspect of the present invention we provide a compound of general formula (I) or a physiologically acceptable salt, solvate or metabolically labile ester thereof for the manufacture of a therapeutic agent for the treatment of the aforementioned diseases, especially hypertension.

According to a further aspect of the present invention we provide a method of treating the aforementioned diseases, especially hypertension, which method comprises administering an effective amount to a patient in need of such treatment of a compound of general formula (I) or a physiologically acceptable salt, solvate or metabolically labile ester thereof.

It will be appreciated that the compounds of general formula (I) or a physiologically acceptable salt, solvate, or metabolically labile ester thereof may advantageously be used in conjunction with one or more other therapeutic agents, such as for example diuretics and/or different antihypertensive agents such as $\beta$-blockers, calcium channel blockers or ACE inhibitors. It is to be understood that such combination therapy constitutes a further aspect of the present invention.

It will be further appreciated that reference herein to treatment extends to prophylaxis as well as to the treatment and relief of established symptoms.

While it is possible that a compound of general formula (I) may be administered as the raw chemical it is preferable to present the active ingredient as a pharmaceutical formulation.

The compounds of general formula (I) and their physiologically acceptable salts, solvates and metabolically labile esters may be formulated for administration in any convenient way, and the invention also includes within its scope pharmaceutical compositions comprising at least one compound of general formula (I) or a physiologically acceptable salt, solvate or metabolically labile ester thereof adapted for use in human or veterinary medicine. Such compositions may be presented for use in conventional manner in admixture with one or more physiologically acceptable carriers or excipients. The carrier(s) must be 'acceptable' in the sense of being compatible with the other ingredients of the formulation and not deleterious to the recipient thereof.

Thus, the compounds according to the invention may be formulated for oral, buccal, parenteral or rectal administration or in a form suitable for administration by-inhalation or insufflation. oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan monooleate; non-aqueous vehicles (which may include edible oils), for example, propylene glycol or ethyl alcohol; and preservatives, for example, methyl or propyl p-hydroxybenzoates or sorbic acid. The compounds or their salts or esters may also be formulated as suppositories, e.g. containing conventional suppository bases such as cocoa butter or other glycerides. For buccal administration the composition may take the form of tablets or lozenges formulated in conventional manner.

It will be appreciated that both tablets and capsules may be manufactured in the form of sustained release formulations, such that they provide a controlled continuous release of the compounds according to the invention over a period of hours.

The compounds of general formula (I) and their physiologically acceptable salts, solvates and metabolically labile esters may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoro methane, dichlorotetrafluoroethane or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, when the compositions comprise dosage units, each unit will preferably contain 5 mg to 500 mg, advantageously where the compounds are to be administered orally 25 mg to 400 mg of the active compound. The daily dosage as employed for adult human treatment will preferably range from 5 mg to 3 g, most preferably from 25 mg to 1 g which may be administered in 1 to.4 daily doses.

The compounds of the invention may be prepared by a number of processes as described below wherein the various groups are as defined for general formula (I) unless otherwise specified. It will be appreciated that in the processes described below, reactive groups may conveniently be protected and deprotected as described herein.

Thus, according to a further aspect of the present invention we provide a process (A) for preparing the compounds of general formula (I) which comprises treating a compound of general formula (II)

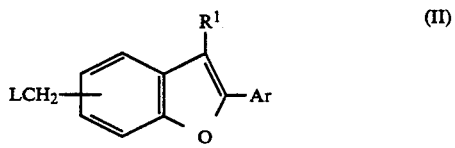

(wherein L is a leaving group, for example a halogen atom such as chlorine, bromine or iodine, or a hydrocarbylsulphonyloxy group such as methanesulphonyloxy, or p-toluenesulphonyloxy and $R^1$ and Ar are as defined in general formula (I)) with an imidazole of formula (III)

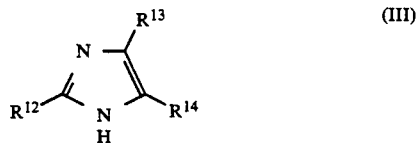

(wherein $R^{12}$ represents a hydrogen atom or a group selected from $C_{1-6}$alkyl, $C_{2-6}$ alkenyl, $C_{1-6}$alkylthio, $C_{1-6}$alkoxy, $C_{3-7}$cycloalkyl or $C_{3-7}$cycloalkyl$C_{1-4}$alkyl; $R^{13}$ and $R^{14}$ which may be the same or different each independently represent a hydrogen or halogen atom, or a group selected from cyano, nitro, $C_{1-6}$alkyl, $C_{2-6}$alkenyl, fluoro$C_{1-6}$alkyl, $C_{3-7}$cycloalkyl, $C_{3-7}$cycloalkyl$C_{1-4}$alkyl, $-(CH_2)_mR^6$, $-(CH_2)_nCOR^7$, $-(CH_2)_pNR^8COR^9$; and $R^6$, $R^7$, $R^8$, $R^9$, m, n and p are as defined in general formula (I)) followed by the removal of any protecting groups where present, as described hereinafter.

The reaction is preferably effected under basic conditions, for example, in the presence of sodium hydride, potassium carbonate or sodium methoxide. The reaction is conveniently effected in a solvent such as acetonitrile or an ether e.g. tetrahydrofuran or dioxan, a ketone e.g. butanone or methyl isobutyl ketone, or a substituted amide e.g. dimethylformamide, at a temperature between 0° C. and the reflux temperature of the solvent.

The intermediate compounds of general formula (II) and their acid addition salts are novel compounds and form a further aspect of the present invention.

In another general process (B) a compound of general formula (I) may be obtained by deprotection of a protected intermediate of general formula (IV)

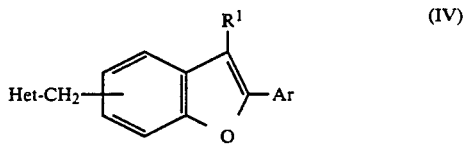

(wherein $R^1$, Ar and Het are as defined in general formula (I) except that at least one reactive group is blocked by a protecting group).

The protecting groups may be any conventional protecting groups, for example as described in "Protective Groups in organic Synthesis" by Theodora Greene (John Wiley and Sons Inc., 1981). Examples of carboxyl protecting groups include $C_{1-6}$ alkyl such as methyl or t-butyl, or $C_{7-10}$ aralkyl such as benzyl.

Deprotection to yield the compound of general formula (I) may be effected using conventional techniques. Thus, for example, aralkyl groups may be cleaved by hydrogenolysis in a suitable organic solvent such as an alcohol, e.g. ethanol, in the presence of a noble metal catalyst such as palladium or platinum or an oxide thereof on a support such as charcoal, and conveniently at room temperature and pressure. Carboxyl protecting groups such as alkyl groups may be cleaved by hydrolysis using a base such as an alkali metal hydroxide (e.g. sodium hydroxide or potassium hydroxide) in a suitable solvent (e.g. an aqueous alcohol such as methanol or ethanol) at any suitable temperature up to reflux. Deprotection, for example, of a tetrazole group when protected with a trityl group may be effected by acid hydrolysis using trifluoroacetic acid or a mineral acid such as hydrochloric acid in a suitable solvent such as ethanol conveniently at room temperature. Alternatively, when possible, deprotection of a tetrazolyl group can be effected by catalytic hydrogenation as previously described.

In another general process (C) a compound of general formula (I) in which the substituent $R^3$ in the group Ar represents $-CONHSO_2R^{17}$ may be prepared from a compound of formula (Ia)

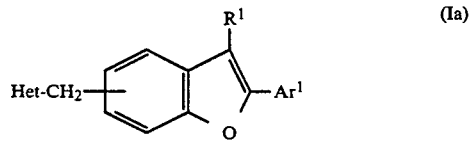

(wherein Het and $R^1$ are as defined in general formula (I) and $Ar^1$ is a group of formula

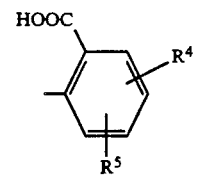

or a protected derivative thereof, in which $R^4$ and $R^5$ are as previously defined) by reaction with a compound of formula $R^{17}SO_2NH_2$ in the presence of a coupling agent such as carbonyldiimidazole and optionally in the presence of a catalyst such as 1,8-diazabicyclo[5.4.0]undec-7-ane (DBU). The reaction is conveniently effected in a solvent such as a substituted amide e.g. dimethylformamide, an ether e.g. tetrahydrofuran, or a halogenated hydrocarbon e.g. dichloromethane at a temperature between 0° C. and 100° C. and conveniently at room temperature.

Alternatively, the acid of formula (Ia) may be converted to an acyl halide under standard conditions, for example, using refluxing thionyl chloride, or using oxalyl chloride in the presence of a base such as triethylamine at a temperature between 0° C. and −50° C., and then treated with an alkali metal salt of $R^{17}SO_2NH_2$ (e.g. the sodium or lithium salt) conveniently at a temperature between −10° C. and +80° C.

In another general process (D) a compound of general formula (I) in which the substiuent $R^3$ in the group Ar represents $—SO_2NHR^{16}$ or $—SO_2NH$-heteroaryl may be prepared from a compound of formula (Ib)

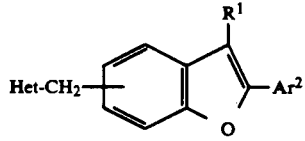

(wherein Het and $R^1$ are as defined in general formula (I) and $Ar^2$ represents a group of formula

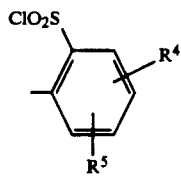

in which $R^4$ and $R^5$ are as previously defined) by reaction with a compound of formula $H_2NR^{16}$ or $H_2N$-heteroaryl thus, for example, where $R^3$ represents $—SO_2NH_2$, a compound of formula (Ib) may be reacted with aqueous ammonia in an inert solvent (or with dry powdered ammonium carbonate) to form the desired compound.

Similarly, in another general process (E) a compound of general formula (I) in which the substituent $R^3$ in the group Ar represents $—CH_2SO_2NHCOR^{17}$ or $—CH_2SO_2NH$-heteroaryl may be prepared from a compound of formula (Ic)

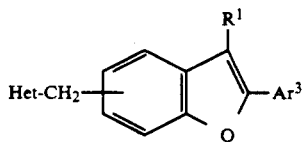

(wherein Het and $R^1$ are as defined in general formula (I) and $Ar^3$ represents a group of formula

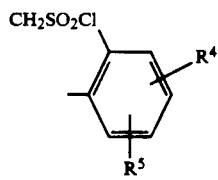

in which $R^4$ and $R^5$ are as previously defined) by reaction with a compound of formula $H_2NCOR^{17}$ or $H_2N$-heteroaryl or, where $R^3$ represents $—CH_2SO_2NHCOR^{17}$, by reaction with ammonia followed by acylation with a compound of formula $R^{17}COX$ (where X is a leaving group such as a halogen atom, e.g. chlorine or bromine) under standard conditions.

In another general process (F) a compound of general formula (I) in which the substituent $R^3$ in the group Ar represents

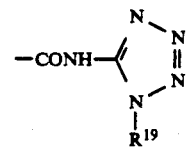

may be prepared by reacting a compound of formula (Ia) with a 5-amino-tetrazole intermediate under standard conditions of amide formation, for example, as described above in general process (C). It will be appreciated that other methods of amide synthesis may be utilized, for instance, using a peptide-condensing agent such as [(dimethylaminopropyl)ethyl]carbodiimide or dicyclohexylcarbodiimide (DCC) and a suitable additive to form a leaving group, for example, hydroxybenzotriazole.

It will be appreciated that compounds of general formula (I) may also be prepared by interconversion of other compounds of general formula (I), thus for example, where $R^3$ represents $—SO_2NH_2$, this group may be converted into the group $—SO_2NHCOR^{17}$ or $—SO_2NHCONHR^{17}$ using standard conditions of amide formation as described above in general process (C).

In the processes (A), (B), (C), (D), (E) and (F) described above, the compounds of general formula (I) may be obtained in the form of a salt, conveniently in the form of a physiologically acceptable salt. Where desired, such salts may be converted into the corresponding free acids or free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

The intermediate compounds of general formula (II) may be prepared from a compound of formula (V):

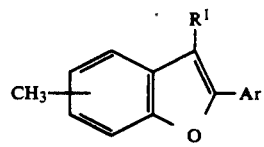

using any suitable reagent well known in the art for converting the methyl on the 6-membered ring into the group $—CH_2L$ (wherein L is as defined above). Thus, for example, when L is a halogen atom, a compound of formula (V) can be converted into a compound of general formula (II) using N-chloro amides, tert-butyl hypochlorite or N-bromosuccinimide. Halogenation of the side chain may be catalysed by light, thus the reaction can be illuminated with a suitable artificial light source, and preferably in the presence of a free radical initiator such as azobisisobutyronitrile (AIBN) or benzoyl peroxide.

Compounds of formula (V) wherein $R^1$ is a halogen atom, for example, a bromine atom, may be prepared by halogenation of a compound of formula (V) wherein $R^1$ represents a hydrogen atom, using for example, bromine, in a suitable solvent such as a halogenated hydrocarbon, e.g. carbon tetrachloride.

Compounds of formula (V) may be prepared by reaction of a compound of formula (VI)

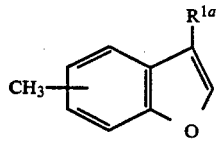
(VI)

(wherein $R^{1a}$ represents a hydrogen atom or a group selected from $C_{1-6}$ alkyl, $C_{2-6}$ alkenyl or fluoro$C_{1-6}$ alkyl) with a compound of formula (VII)

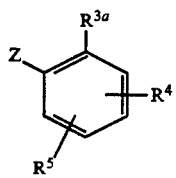
(VII)

(wherein Z represents a bromine or iodine atom or the group $-OSO_2CF_3$, $R^4$ and $R^5$ are as defined in general formula (I) and $R^{3a}$ is as defined for $R^3$ in general formula (I) or is a protected derivative or precursor thereof).

The compound of formula (VI) is first treated with an alkyl lithium compound such as n-butyl lithium at a reduced temperature, for example, between $-100°$ C. and $0°$ C. in a solvent such as an ether (e.g. tetrahydrofuran). The mixture is then treated with a trialkylborate compound such as triisopropylborate and the temperature conveniently brought up to room temperature. Subsequently, water may be added and the mixture treated with a mineral acid such as sulphuric acid thus producing a compound of formula (VIa)

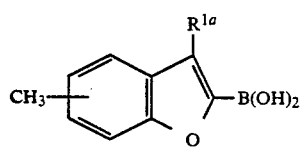
(VIa)

The intermediate compound of formula (VIa) is then reacted with a compound of formula (VII) in the presence of a palladium (0) compound such as tetrakis(triphenylphosphine) palladium (0) in a solvent such as an ether (e.g. dimethoxyethane), and in the presence of a base such as sodium carbonate or thallium hydroxide. The reaction is conveniently effected at an elevated temperature, such as the reflux temperature of the solvent.

Compounds of formula (V) may also be prepared by an intramolecular cyclisation reaction of a compound of formula (VIII)

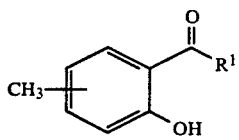
(VIII)

(wherein $R^1$ is as previously defined with the exception of CHO, $COR^2$, where $R^2$ is $C_{1-6}$alkoxy or $-NR^{10}R^{11}$, and halogen) with a suitably substituted benzene of formula (IX)

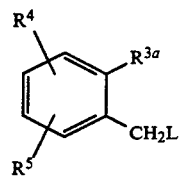
(IX)

(wherein L and $R^{3a}$ are as previously defined) in the presence of a base such as sodium hydride or potassium carbonate. The cyclisation is a two step reaction which requires one equivalent of base per step. It will be appreciated however that the reaction can be effected in the presence of two equivalents of base to avoid the need to isolate the intermediate. The reaction is conveniently effected in a solvent such as an ether e.g tetrahydrofuran, an alcohol e.g ethanol or a substituted amide e.g dimethylformamide, at a temperature between room temperature and the reflux temperature of the solvent.

It will be appreciated that compounds of formula (V) in which $R^1$ represents a hydrogen or halogen atom may also be converted into compounds of formula (V) in which $R^1$ represents the group methyl (via hydrogenolysis of the Mannich base), $-CHO$ or $-COR^2$ (wherein $R^2$ is as defined in general formula (I)) using techniques well known in the art, such as those described in "Heterocyclic Chemistry" by J. A. Joule and G. F. Smith, Van Nostrand Reinhold Company, London (1972), "Heterocyclic Chemistry" by A. Albert, 2nd Edition, The Athlone Press, London (1968), "Heterocyclic compounds", Vol. 29 by A. Mustafa, John Wiley and Sons Inc., New York (1974), "Heterocyclic Compounds", Vol. 2 by R. C. Elderfield, John Wiley and Sons Inc., New York (1951) and "Advances in Heterocyclic Chemistry", Vol. 29 by A. R. Katritsky and A. J. Boulton, Acadermic Press, New York (1981).

Compounds of formulae (Ia), (Ib) and (Ic) may be made in a similar manner to that described in general process (A) using an intermediate of formula (X)

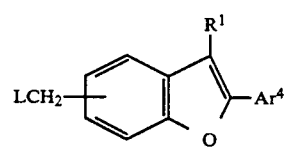
(X)

(wherein $R^1$ is as defined in general formula (I), L is as defined in general formula (II) and $Ar^4$ is a group of formula

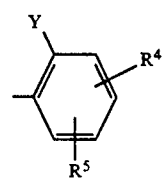

in which $R^4$ and $R^5$ are as previously defined, and Y is a group selected from $-CO_2H$, or a precursor of $-SO_2Cl$ and $-CH_2SO_2Cl$ such as $SO_2H$ and $CH_2SO_2H$).

Compounds of formula (X) may be prepared by processes analogous to those described herein above from a compound of formula (XI)

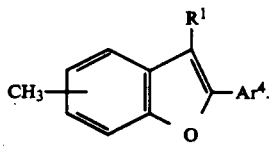
(XI)

The intermediates of formula (XI) may be prepared from a compound of formula (VI) and an appropriate benzene derivative of formula (XII)

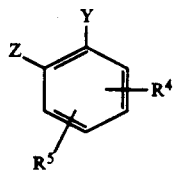
(XII)

using the method described above for the preparation of a compound of formula (V).

Where $R^{3a}$ or Y represents —SO$_2$Cl, this group may be prepared from a corresponding compound wherein $R^{3a}$ or Y represents —NH$_2$ by reaction with sodium nitrite in the presence of a mineral acid such as hydrochloric acid to form an aromatic diazonium chloride salt, followed by treatment with sulphur dioxide in the presence of a copper (II) salt such as a copper chloride to form the group —SO$_2$Cl.

Where $R^{3a}$ or Y represents —CH$_2$SO$_2$Cl, this group may be prepared from a corresponding compound wherein R or Y represents —CH$_2$Cl firstly by formation of the Grignard reagent where $R^{3a}$ or Y represents —CH$_2$MgCl using standard conditions, followed by reaction with sulphuryl chloride.

The imidazoles of formula (III) may be prepared as described in European specification No. 0253310A and in U.S. Pat. No. 4,355,040 or by methods analogous to those described therein. The content of these references is hereby incorporated by reference.

Intermediates of formulae (VI), (VII), (VIII), (IX) and (XII) are either known compounds or may be prepared by methods analogous to those used for the preparation of the known compounds.

The following examples illustrate the invention. Temperatures are in °C. "Dried" refers to drying using magnesium sulphate. Thin layer chromatography (t.l.c.) was carried out on silica and column chromatography was carried out on silica (Merck 9385 unless otherwise stated), using one of the following solvent systems : A—ether:hexane, B—ether: dichloromethane, C—dichloromethane:ethanol:ammonia, D-dichloromethane:ethyl acetate, or E-dichloromethane:ether:acetic acid. The following abbreviations are used : THF—tetrahydrofuran; DME—dimethoxyethane; AIBN—azobisisobutyronitrile; DMF—dimethylformamide; THEDA— tetramethylethylenediamine; NBS—N-bromosuccinimide; DMAP—4-dimethylaminopyridine; DEAD—diethyl azodicarboxylate.

Intermediate 1

5-Methylbenzofuran-2-boronic acid n-Butyl lithium (35.16 ml) was added dropwise to a stirred solution of THEDA (9.58 ml) and 5-methylbenzofuran (8.22 g) in ether (250 ml) maintaining the temperature below −60° C. throughout. The solution was warmed to about −10° C. over 45 minutes and stirred at this temperature for 30 minutes. A precipitate formed on warning. The suspension was cooled and triisopropylborate (43 ml) was added, maintaining the temperature below −60° C. The solution was warmed gradually to room temperature before quenching with 2N HCl (70 ml). The mixture was extracted with ether (3×50 ml) and the combined organic extracts washed with 2N HCl (4×30 ml), water (2×30 ml) and dried before evaporation to give the title compound as an orange solid (12.75 g).

t.l.c. System A (1:1), Rf 0.3.

Intermediate 2

Methyl 2-(5-methyl-2-benzofuranyl)benzoate

A solution of methyl 2-bromobenzoate (11.70 g), Intermediate 1 (12.75 g) and tetrakistriphenylphosphine palladium (0) (0.5 g) in DME (300 ml) and 2N Na$_2$CO$_3$ (60 ml) was heated to reflux with vigorous stirring under nitrogen. After 1.5 h a further 500 mg of catalyst was added and stirring at reflux under nitrogen continued. After about 5 h the reaction was cooled to room temperature and diluted with ether (300 ml). The organic layer was separated and washed with water (3×100 ml) and dried. Filtration and evaporation gave a yellow oily suspension (19.27 g) which was purified by chromatography eluting with System A (1:9) to give a yellow oil (11.06 g). This was further purified by Kugelrohr distillation to give the title compound (4.31 g).

t.l.c. System A (1:9), Rf 0.5.

Intermediate 3

Methyl 2-(3-bromo-5-methyl-2-benzofuranyl)benzoate

A solution of Intermediate 2 (0.25 g) in carbon tetrachloride (5 ml) was cooled to −20° C. and treated dropwise with in bromine in carbon tetrachloride (0.7ml). stirring at −20° C. was then continued for 1 h before gradual warming to room temperature. Stirring at room temperature was continued overnight. Cyclohexene (0.1 ml) was added dropwise and the solvents were evaporated in vacuo to give the title compound as an orange oil (0.26 g).

t.l.c. System A (1:9), Rf 0.45.

Intermediate 4

2-(3-Bromo-5-methyl-2-benzofuranyl)benzoic acid

A solution of Intermediate 3 (2.20 g) in methanol (20 ml) was treated with sodium hydroxide (2N;3 ml). The solution was heated to reflux and heating was continued for 3 h. The solvent was removed in vacuo and the residue diluted with water- The basic aqueous phase was washed with ether (3×30 ml) before acidification to pH-2 using 2N HCl. A white suspension formed. This was extracted with ether (4×20 ml) and the combined organic extracts dried, filtered and evaporated to give the title compound as a pale yellow solid (1.93 g).

T.l.c. ether, Rf 0.7

Intermediate 5

Phenylmethyl 2-(3-bromo-5-methyl-2-benzofuranyl)benzoate

A solution of DEAD (7.51 g) in THF (50 ml) was added dropwise to a stirred solution of Intermediate 4

(8.35 g) in THF (200 ml) containing triphenylphosphine (11.9 g) and benzyl alcohol (2.86 ml, 2.99 g). After stirring overnight, the solution was partitioned between ethyl acetate (200 ml) and water (200 ml) and the separated organic phase washed with water (200 ml), dried and concentrated in vacuo to afford an orange oil (26.5 g). Purification by column chromatography (Merck 7734) eluting with System A (1:4) afforded the title compound as a pale yellow gum (8.9 g).

T.l.c. System A (1:1) Rf=0.55

Intermediate 6

Phenylmethyl 2-[3-bromo-5-(bromomethyl)-2-benzofuranyl]benzoate

NBS (2.03 g) and dibenzoyl peroxide (0.1 g) were added to a stirred solution of Intermediate 5 (4.3 g) in carbon tetrachloride (200 ml). After stirring at reflux for 1 h, further NBS (0.6 g) was added and heating continued for a further 1 h. After standing overnight at room temperature, the suspension was filtered and the filtrate concentrated in vacuo to afford an orange oil (8.2 g). Purification by column chromatography (Merck 7734) eluting with System A (1:9) afforded the title compound a as pale yellow gum (1.45 g).

T.l.c. System A (1:1) Rf=0.5

Intermediate 7

2-Butyl-4-chloro-1H-imidazole-5-carboxaldehyde

A suspension of 2-butyl-4-chloro-1H-imidazole-5-methanol (22.0 g) in dichloromethane:1,4-dioxan (2:1) (690 ml) was treated with manganese dioxide (63.15 g) and the reaction mixture heated at reflux under nitrogen for 3.5 h. The reaction mixture was cooled, filtered and the filtrate evaporated to leave an off-white solid. The residue was triturated with petroleum ether, filtered and dried to give the title compound as a white solid (17.9 g) m.p. 98°–99° C.

Intermediate 8

Phenylmethyl 2-[3-bromo-5-[(2-butyl-4-chloro-5-formyl-1H-imidazol-1-yl)methyl]-2-benzofuranyl)benzoate A solution of Intermediate 6 (1.90 g) in DMF (15 ml) was added dropwise to a stirred suspension of Intermediate 7 (0.67 g) and anhydrous potassium carbonate (0.59 g) in DMF (40 ml) under nitrogen. After stirring for 20 h at room temperature, the solution was partitioned between ethyl acetate (50 ml) and water (70 ml). The separated aqueous phase was further extracted with ethyl acetate (50 ml) and the combined organic extracts washed with water (4×70 ml), dried and concentrated in vacuo to afford an orange oil (2.24 g). Purification by column chromatography (Merck 7734) eluting with System A (1:6→1:2) afforded a colourless oil which was further purified by column chromatography (Merck 7734) eluting with System-C (300:8:1) to give the title compound as a white foam (1.47 g)

T.l.c System C (300:8:1) Rf=0.4

Intermediate 9

2-Butyl-4-chloro-1-[[3-bromo-2-[2-[(phenylmethoxy)-carbonyl]phenyl]-5-benzofuranyl]methyl]-1H-imidazole-5-carboxylic acid A solution of sodium chlorite (80% tech, 1.34 g) and sodium dihydrogen orthophosphate (1.49 g) in water (20 ml) was added to a mixture of Intermediate 8 (1.45 g) and 2-methylbut-2-ene (2M in THF, 10 ml) in THF (35 ml) and t-butanol (20 ml). The mixture was vigorously stirred for 20 h and partitioned between ethyl acetate (30 ml) and water (40 ml). The separated aqueous phase was further extracted with ethyl acetate (40 ml) and the combined organic extracts washed with water (2×50 ml), dried and concentrated in vacuo to afford a colourless oil (1.65 g). Purification by column chromatography eluting with ether→ether:acetic acid (99:1) gave the title compound (1.44 g) as a brown foam.

N.m.r (DMSOd₆) δ0.82 (t,3H), 1.3 (m,2H), 1.58 (m,2H), 2.69 (t,2H), 5.15 (s,2H), 5.8 (s,2H), 7.0–7.3 (m,7H). 7.58 (d,1H) 7.7–7.85 (m,3H), 8.0 (d,1H)

Intermediate 10

Ethyl 2-butyl-4-chloro-1-[[3-bromo-2-[2-[(phenylmethoxy)-carbonyl]phenyl]-5-benzofuranyl]methyl]-1H-imidazole-5-carboxylate A solution of DEAD (0.41 g) in THF (20 ml) was added dropwise to a stirred solution of the product of Intermediate 9 (0.73 g) and triphenylphosphine (0.645 g) in ethanol (0.7 ml) and THF (20 ml). After stirring at room temperature for 16 h, the solution was concentrated in vacuo to afford a yellow gum (2.22 g). Purification by chromatography eluting with a gradient of System A (1:4) increasing to (1:1) afforded the title compound (0.75 g) as a colourless gum.

T.l.c. System-A (1:1) Rf 0.5

N.m.r. (CDCl₃) δ0.9 (t,3H), 1.35 (m,5H), 1.75 (m,2H), 2.7 (t,2H), 4.3 (q,2H), 5.15 (s,2H), 5.65 (s,2H), 6.95 (d,2H), 7.1–7.3 (m,6H), 7.5–7.75 (m,3H), 8.0 (d,1H)

Intermediate 11

2-[3-Bromo-5-[(2-butyl-4-chloro-5-(ethoxycarbonyl)-1H-imidazol-1-yl)methyl]-2-benzofuranyl]benzoic acid A solution of Intermediate 10 (0.42 g) and 1N hydrochloric acid (0.7 ml) in absolute ethanol (40 ml) containing 5% palladium on carbon (50% paste; 0.138 g) was hydrogenated at room temperature and pressure for 1 h. The reaction mixture was filtered and the filtrate concentrated in vacuo to afford a colourless gum (0.383 g). Purification by column chromatography (Merck 7734) eluting with ether:hexane:acetic acid (250:250:1) followed by concentration in vacuo and azeotroping with toluene (30 ml) gave the title compound as a white solid (0.242 g).

m.p. 179°–181° C.

Analysis Found: C,55.9; H,4.3; N,4.85;
$C_{26}H_{24}BrClN_2O_5$ requires: C,55.8; H,4.3; N,5.0%

Intermediate 12

1,1-Dimethylethyl 2-(3-bromo-5-methyl-2-benzofuranyl)benzoate

The title compound was prepared from Intermediate 1 and 1,1-dimethylethyl 2-bromobenzoate according to the method of Intermediate 2, followed by bromination according to the method of Intermediate 3.

T.l.c. dichloromethane:hexane (1:2) Rf=0.3

Intermediate 13

1,1-Dimethylethyl 2-[3-bromo-5-(bromomethyl)-2-benzofuranyl]benzoate

The title compound was prepared from Intermediate 12 according to the method of Intermediate 6.

t.l.c. System A (1:10) Rf=0.4

Intermediate 14

Ethyl α-amino-β-oxocyclopropanepropanoate hydrochloride

Acetyl chloride (15.35 ml, 16.88 g) was added to a cooled solution of ethyl α-(hydroxyimino-3-oxocyclopropanepropanoate (20 g) in absolute ethanol (250 ml) before being added to a suspension of 5% platinum on carbon (1.85 g) in absolute ethanol (150 ml). The stirred mixture was then hydrogenated at room temperature and pressure for 5 h. The catalyst was filtered off through a pad of hyflo and the filtrate concentrated in vacuo to give, after azeotroping with toluene (2×80 ml), an off-white solid. This was triturated with ether (500 ml) to give the title compound (14.5 g) as a white solid. m.p. 196°–197° C.

Intermediate 15

Ethyl 4-cyclopropyl-2-ethyl-1H-imidazole-5-carboxylate

A solution of Intermediate 14 (14.5 g) in absolute ethanol (110 ml) was added dropwise over 1 h to a stirred suspension of ethyl propaniniidate hydrochloride (25.1 g) and triethylamine (32 ml, 22.7 g) in absolute ethanol (200 ml). After stirring overnight under nitrogen, the grey suspension was concentrated in vacuo to afford a grey residue which was partitioned between ethyl acetate (250 ml), ethanol (50 ml), water (200 ml) and brine (100 ml). The aqueous phase was further extracted with ethyl acetate (2×100 ml) and the combined organic extracts were dried and concentrated in vacuo to afford a grey solid (31 g). Purification by chromatography eluting with System A (1:3) increasing to (1:1) gave the title compound (3.5 g) as a white solid m.p. 154°–155° C.

Intermediate 16

Ethyl 1-[[3-bromo-2-[2-[(1,1-dimethylethoxy)carbonyl]-phenyl]-5-benzofuranyl]methyl]-4-cyclopropyl-2-ethyl-1H-imidazole-5-carboxylate A solution of Intermediate 13 (14.5 g) and Intermediate 15 (5 g) in dry DMF (100 ml) and anhydrous potassium carbonate (4.15g) was vigorously stirred at room temperature for 48h. The mixture was diluted with ethyl acetate (240 ml) and washed with lithium chloride (2×200 ml and 2×80 ml). The organic solution was dried and evaporated to leave a yellow solid which was triturated with ether (50 ml) to give the title compound as an off-white solid (11 g). T.l.c. System A (1:1) Rf=0.3.

Intermediate 17

Ethyl 1-[[3-bromo-2-(2-carboxyphenyl)-5-benzofuranyl]methyl]-4-cyclopropyl-2-ethyl-1H-imidazole-5-carboxylate A solution of Intermediate 16 (1.25 g) in trifluoroacetic acid (9 ml) was stirred at room temperature for 4 h. The solvent was evaporated in vacuo. The residue was dissolved in water (50 ml) and the pH adjusted to between 4 and 5 with aqueous sodium carbonate solution. The product was extracted with a mixture of ethyl acetate:dichloromethane:methanol (100:100:5) and the extract evaporated to give a solid residue. The residue was crystallised, from methanol:water to give the title compound as an off-white solid (0.85 g)
T.l.c. dichloromethane:methanol (10:1) Rf=0.45.

EXAMPLE 1

Ethyl 1-[[3-bromo-2-[2-[[(1H-tetrazol-5-yl)aminolcarbonyl]-phenyl]-5-benzofuranyl]methyl]-2-butyl-4-chloro-1H-imidazole-5-carboxylate A mixture of Intermediate 11 (179 mg) and hydroxybenzotriazole (50 mg) in dry DMF at 0° C. was treated with [(dimethylamino)propyl]ethyl carbodiimide hydrochloride (75 mg) and stirred for 20 min. 5-Aminotetrazole (34 mg) and dry ethylamine (0.05 ml) were added and stirring was continued at ambient temperature for 20 h. The reaction mixture was diluted with ethyl acetate (10 ml), washed with water (10 ml), dilute HCl (pH3–4), 10% lithium chloride solution (2×10 ml), dried and evaporated. The residue was purified by flash chromatography using ethyl acetate/hexane/acetic acid (100:100:4) as the eluant to give the title compound as a white solid (72 mg).

T.l.c. Ethyl acetate/Hexane/Acetic acid (100:100:4), Rf 0.3

Mass Spec: MH+(calc.) 598; MH+(obs.) 598

EXAMPLE 2

1-[[3-Bromo-2-[2-[[(1H-tetrazol-5-yl)amino]carbonyl]-phenyl]-5-benzofuranyl]methyl]-2-butyl-4-chloro-1H-imidazole-5-carboxylic acid A mixture of the product of Example 1 (65 mg), methanol (2.5 ml) and aqueous sodium hydroxide solution (1M; 0.4 ml) was heated at 40° C. for 20 h. Hydrochloric acid (1M) was added and the resulting precipitate was collected by filtration to give the title compound as a white solid (41 mg).

T.l.c. Ethyl acetate/Hexane/Acetic acid (100:100:4), Rf 0.19

Mass Spec: MH+(calc.) 598; RH+(obs.) 598

EXAMPLE 3

Ethyl 1-[[3-bromo-2-[2-[[(phenylsulphonyl)amino]carbonyl]-phenyl]-5-benzofuranyl]methyl]-4-cyclopropyl-2-ethyl-1H-imidazole-5-carboxylate A solution of Intermediate 17 (0.630 g) and 1,1'-carbonyldiimidazole (0.23 g) in dry THF (20 ml) was stirred at ambient temperature for 5 h. Benzenesulphonamide (O.+8 g) and 1,8-diazabicyclo[5.4.0]undec-7-ene (0.24 ml) were added and the mixture was heated at reflux for 56 h. The solvent was evaporated in vacuo, the residue was dissolved in dichloromethane (50 ml), washed with water (50 ml) (pH adjusted to 4 with hydrochloric acid 2M), dried and evaporated. The residue was purified by column chromatography eluting with dichloromethane:methanol (20:1) to give the title compound as an off-white foam (647 mg)

T.l.c. dichloromethane:methanol (10:1) Rf 0.7
Mass Spec: MH+(calc.) 676; MH+(obs.) 676

EXAMPLE 4

1-[[3-Bromo-2-[2-[[(phenylsulphonyl)amino]carbonyl]phenyl]-5-benzofuranyl]methyl]-4-cyclopropyl-2-ethyl-1H-imidazole-5-carboxylic acid A solution of the product of Example 3 (0.57 g) in methanol (10 ml) and aqueous sodium hydroxide solution (2M; 2.5 ml) was heated at 60° for 4 h. The organic solvent was evaporated in vacuo and the residue was acidified with hydrochloric acid (2M; 2.5 ml). The precipitate was collected by filtration to give the title compound as a white solid (0.453 g), m.p. 176°-8°.

T.l.c. dichloromethane:methanol (10:1) Rf 0.5.

EXAMPLE 5

1-[[3-Bromo-2-[2-[[(phenylsulphonyl)amino]carbonyl]-phenyl]-5-benzofuranyl]methyl]-4-cyclopropyl-2-ethyl-1H-imidazole-5-carboxamide A mixture of the product of Example 4 (0.2 g) and 1,1'-carbonyldiimidazole (0.06 g) in dry dichloromethane (50 ml) was stirred at ambient temperature for 8 h. 0.88 Ammonia (2 ml) was added and the mixture was stirred at ambient temperature for 18 h. The solvent was evaporated and the residue was dissolved in dichloromethane (50 ml) and washed with water (50 ml) (pH adjusted to 5 with hydrochloric acid). The organic solution was dried, filtered and evaporated to give a semi-solid residue. The residue was purified by column chromatography eluting with dichloromethane:methanol (10:1), followed by crystallization from ethyl acetate/methanol to give the title compound as a white solid (40 mg), m.p. 285° C. dec.

T.l.c. dichloromethane:methanol (10:1) Rf 0.5

The compounds of the invention are tested in vitro for angiotensin II receptor antagonism. Aortic strips are obtained from male New Zealand white rabbits and prepared for recording isometric contractions in response to cumulative addition of angiotensin II. The potencies of test antagonists are assessed by measuring their abilities to displace the angiotensin II cumulative concentration response curve. The method used is that of Ackerly et al., *Proc. Natl. Acad. Sci.*, 74(12), pp5725-28 (1977) with the exception that the final composition of the physiological salt solution is as given below in Table 1:

TABLE 1

| Ingredient | Amount (mM) |
|---|---|
| $Na^+$ | 143.4 |
| $K^+$ | 5.9 |
| $Mg^{2+}$ | 0.6 |
| $Ca^{2+}$ | 1.3 |
| $Cl^-$ | 124.5 |
| $HPO_4^-$ | 1.2 |
| $SO_4^{2-}$ | 0.6 |
| $HCO_3^-$ | 25.0 |
| glucose | 11.1 |
| indomethacin | 0.005 |
| ascorbic acid | 0.1 |

The tissues are initially challenged with K+ (80 mM) and then washed at 0, 5, 10 and 15 minutes after the response to K+ has plateaued. After a further 45 minutes an angiotensin II cumulative response curve is constructed (0.1 nM to 0.1 μm in 10-fold increments) and the tissues are washed as before. A second, third and fourth angiotensin II cumulative response curve (0.1 nM to 0.1 μm in 3-fold increments) is then constructed at hourly intervals (15 minutes washing after each curve followed by 45 minutes equilibration). The compounds of the invention (30 μM) are tested for angiotensin II receptor antagonism by application 45 minutes before construction of the fourth angiotensin II curve. The third and fourth angiotensin II curves are expressed graphically and a concentration ratio (CR) is calculated by dividing the angiotensin II $EC_{50}$ value obtained in the presence of the test antagonist (i.e. fourth curve) by the angiotensin II $EC_{50}$ value obtained in the absence of the test antagonist (i.e. third curve).

The potency of the test antagonist is expressed as a pKb which is calculated from the equation:

$$pKb = -\log\left[\frac{CR - 1}{[\text{antagonist}]}\right]$$

which is a rearrangement of equation 4 described by Furchgott, in *Handbook of Exp. Pharmacol.*, 33, p290 (1972) (eds. Blaschko and Muscholl).

If a compound supresses the maximum response to angiotensin II, a pKb is estimated using the double reciprocal plot technique for insurmountable antagonists, described by T. P. Kenakin, *Pharmacol. Rev.*, 36(3), pp165-222 (esp. 203-204) (1984).

Compounds of the invention will desirably exhibit a pKb in the range between 5 and 12. Thus we have found that the compounds of the invention inhibit the action of the hormone angiotensin II and are therefore useful in the treatment of conditions in which it is desirable to inhibit angiotensin II activity. In particular, the compounds of the Examples are active in the above test.

There is thus provided as a further aspect of the invention a compound of general formula (I) or a physiologically acceptable salt, solvate or metabolically labile ester thereof for use in the treatment of conditions associated with excessive or unregulated angiotensin II activity.

In a further or alternative aspect of the invention there is provided a compound of general formula (I) or a physiologically acceptable salt, solvate or metabolically labile ester thereof for the manufacture of a therapeutic agent for the treatment of conditions associated with excessive or unregulated angiotensin II activity.

There is also provided in a further or alternative aspect of the invention a method for the treatment of conditions associated with excessive or unregulated angiotensin II activity in a mammal including man comprising administration of an effective amount to a mammal in need of such treatment a compound of general formula (I) or a physiologically acceptable salt, solvate or metabolically labile ester thereof.

In addition, by virtue of their antagonistic activity at angiotensin II receptors, compounds of the present invention will be of value in the treatment of conditions associated with activation of the Renin-Angiotensin System.

There is thus provided a further aspect of the present invention a compound of general formula (I) or a physiologically acceptable salt, solvate or metabolically labile ester thereof for use in the treatment of a condition associated with activation of the Renin-Angiotensin system.

In a further or alternative aspect of the present invention there is provided a compound of general formula (I) or a physiologically acceptable salt, solvate or metabolically labile ester thereof for the manufacture of a therapeutic agent for the treatment of a condition associated with activation of the Renin-Angiotensin System.

There is also provided in a further or alternative aspect of the present inventions a method for the treatment of a condition associated with the activation of the Renin-Angiotensin system in a mammal including man comprising administration of an effective amount to a mammal in need of such treatment of a compound of general formula (I) or a physiologically acceptable salt, solvate or metabolically labile ester thereof.

The following examples illustrate pharmaceutical formulations according to the invention. The term "active ingredient" is used herein to represent a compound of formula (I).

PHARMACEUTICAL EXAMPLE 1

| Oral Tablet A | |
| --- | --- |
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

PHARMACEUTICAL EXAMPLE 2

| Oral Tablet B | |
| --- | --- |
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

PHARMACEUTICAL EXAMPLE 3

| Inhalation Cartridge | |
| --- | --- |
| Active Ingredient | 1 mg |
| Lactose | 24 mg |

Blend active ingredient, particle size reduced to a very fine particle size (weight mean diameter ca. 5KM) with the lactose in a suitable powder blender and fill the powder blender into No. 3 hard gelatin capsules.

The contents of the cartridges may be administered using a powder inhaler.

PHARMACEUTICAL EXAMPLE 4

| Injection Formulation | % w/v |
| --- | --- |
| Active ingredient | 1.00 |
| Water for injections B.P. | to 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of formula (I):

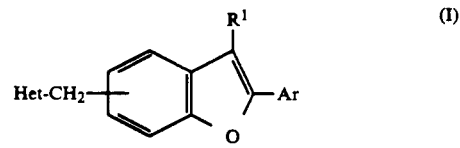

or a physiologically acceptable salt, solvate or metabolically labile ester thereof wherein $R^1$ represents a hydrogen atom or a halogen atom or a group selected from $C_{1-6}$alkyl, $C_{2-6}$alkenyl, fluoro$C_{1-6}$alkyl, $C_{1-6}$alkoxy, —CHO, —CO$_2$H or —COR$^2$;

Ar represents the group

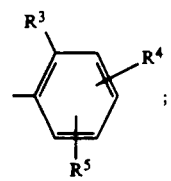

$R^2$ represents a group selected from $C_{1-6}$alkyl, $C_{2-6}$alkenyl, $C_{1-6}$alkoxy or the group —NR$^{10}$R$^{11}$, $R^3$ represents a group selected from —SO$_3$R$^{15}$, —PO(OR$^{15}$)$_2$, —PO(OR$^{16}$R$^{16}$, —SO$_2$NHR$^{16}$, —CONHNHSO$_2$CF$_3$, —SO$_2$NH-heteroaryl, —CH$_2$SO$_2$NH-heteroaryl, —SO$_2$NHCOR$^{17}$, —CH$_2$SO$_2$NHCOR$^{17}$, —CONHSO$_2$R$^{17}$, —CH$_2$CONHSO$_2$R$^{17}$, —NHSO$_2$NHCOR$^{17}$, —NHCONHSO$_2$R$^{17}$, —SO$_2$NHCONHR$^{17}$, —CONHSO$_2$NHR$^{17}$,

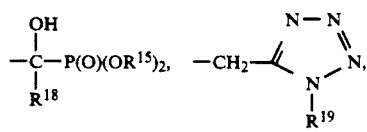

-continued

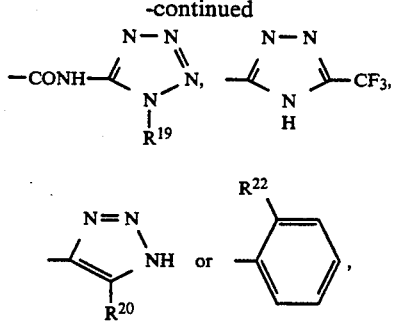

wherein 'heteroaryl' represents a 5 membered aromatic ring containing from 1 to 3 nitrogen atoms said aromatic ring being optionally substituted by 1 or 2 substituents selected from a halogen atom or a group selected from hydroxy, —SH, $C_{1-4}$alkyl, $C_{1-4}$alkoxy, —$CF_3$, —$NO_2$, —$CO_2H$, $C_{1-5}$acyloxy, —$NH_2$, $C_{1-4}$alkylamino or di$C_{1-4}$alkylamino; $R^4$ and $R^5$ which may be the same or different each independently represent a hydrogen atom or a halogen atom or a $C_{1-6}$ alkyl group; Het represents an N-linked imidazolyl group optionally substituted at the 2-position by a $C_{1-6}$alkyl, $C_{2-6}$alkenyl, $C_{1-6}$alkylthio, $C_{1-6}$alkoxy, $C_{3-7}$cycloalkyl or $C_{3-7}$cycloalkyl$C_{1-4}$alkyl group, the imidazolyl group optionally being substituted at the 4-and 5-positions by one or two further substituents selected from a halogen atom or a group selected from cyano, nitro, $C_{1-6}$alkyl, $C_{2-6}$alkenyl, fluoro$C_{1-6}$alkyl, $C_{3-7}$cycloalkyl, $C_{3-7}$cycloalkyl$C_{1-4}$alkyl, $(CH_2)_mR^6$, —$(CH_2)_nCOR^7$ or —$(CH_2)_pNR^8COR^9$;

$R^6$ represents a hydroxy or $C_{1-6}$alkoxy group;

$R^7$ represents a hydrogen atom or a group selected from hydroxy, $C_{1-6}$alkyl, $C_{1-6}$alkoxy, phenyl, phenoxy or the group —$NR^{10}R^{11}$;.

$R^8$ represents a hydrogen atom or a $C_{1-6}$alkyl group;

$R^9$ represents a hydrogen atom or a group selected from $C_{1-6}$alkyl, $C_{1-6}$alkoxy, phenyl, phenoxy or the group —$NR^{10}R^{11}$;

$R^{10}$ and $R^{11}$, which may be the same or different, each independently represent a hydrogen atom or a $C_{1-4}$alkyl group;

$R^{15}$ represents a hydrogen atom or the group —$CH(R^{16})OC(O)R^{21}$;

$R^{16}$ represents a hydrogen atom or a group selected from $C_{1-6}$alkyl, phenyl or benzyl;

$R^{17}$ represents a group selected from aryl, heteroaryl (as defined above), $C_{3-7}$cycloalkyl, perfluoro$C_{1-4}$alkyl or $C_{1-4}$alkyl optionally substituted by a halogen atom or a group selected from hydroxy, —SH, $C_{1-4}$alkyl, $C_{1-4}$alkoxy, $C_{1-4}$alkylthio, —$CF_3$, —$NO_2$, —$CO_2H$, —$C_{1-5}$acyloxy, —$NH_2$, $C_{1-4}$alkylamino, di$C_{1-4}$alkylamino, —$PO_3H$ or —PO(OH)$C_{1-4}$alkoxy, wherein 'aryl' represents a phenyl or naphthalenyl group optionally substituted by 1 or 2 substituents selected from a halogen atom or a group selected from $C_{1-4}$alkyl, $C_{1-4}$alkoxy, —$NO_2$, —$CF_3$, $C_{1-4}$alkylthio, hydroxy or —$NH_2$;

$R^{18}$ represents a hydrogen atom or a group selected from $C_{1-6}$alkyl, phenyl or benzyl;

$R^{19}$ represents a hydrogen atom or a group selected from $C_{1-6}$alkyl, $C_{2-4}$alkenyl or $C_{1-4}$alkoxy$C_{1-4}$alkyl;

$R^{20}$ represents a group selected from —CN, —$NO_2$ or —$CO_2R^{16}$;

$R^{21}$ represents a group selected from $C_{1-6}$alkyl, aryl (as defined above) or —$CH_2$-aryl (as defined above);

$R^{22}$ represents a group selected from —$CO_2R$, —$SO_3R^{15}$, —$NHSO_2CF_3$, —$PO(OR^{15})_2$, —$SO_2NHR^{18}$ or a Clinked tetrazolyl group;

m represents an integer from 1 to 4, preferably 1 or 2, especially 1;

n represents an integer from 0 to 4, preferably 0, 1 or 2, especially 0 or 1; and p represents an integer from 1 to 4, preferably 1 or 2.

2. A compound according to claim 1 wherein Het represents an N-linked imidazolyl group substituted at the 2-position by a hydrogen atom or a $C_{1-5}$alkyl group, preferably a $C_{2-5}$ alkyl group, especially an ethyl, n-propyl or n-butyl group, or a $C_{3-5}$alkenyl group, preferably a but-1-enyl group.

3. A compound according to claim 1 wherein the N-linked imidazolyl group is substituted by one or two further substituents selected from a halogen atom or group selected from $C_{1-6}$alkyl, —$(CH_2)_mR^6$ or —$(CH_2)_nCOR^7$.

4. A compound according to claim 3 wherein the N-linked imidazolyl group is substituted by a halogen atom, preferably a chlorine atom.

5. A compound according to claim 3 wherein the N-linked imidazolyl group is substituted by a group selected from —$(CH_2)_mR^6$ wherein $R^6$ is preferably a hydroxy group or a $C_{1-6}$alkoxy group, especially a methoxy, ethoxy, propoxy or butoxy group, and most preferably a hydroxy or methoxy group, and m represents 1 or 2; or —$(CH_2)_nCOR^7$ wherein $R^7$ is, for example, a hydrogen atom or a group selected from hydroxy, $C_{1-6}$alkoxy, preferably, a methoxy, ethoxy, propoxy or butoxy group, or the group —$NR^{10}R^{11}$ where $R^{10}$ and $R^{11}$ each, preferably, independently represent a hydrogen atom or a $C_{1-4}$alkyl group, and $R^7$ most preferably represents a hydrogen atom, a hydroxy group or a methoxy group, and n preferably represents zero, 1 or 2.

6. A compound according to claim 5 wherein —$(CH_2)_mR^6$ is a group selected from —$CH_2OH$ or —$CH_2OCH_3$; or —$(CH_2)_nCOR^7$ is a group selected from —CHO, —$CO_2H$, —$CO_2CH_3$, —$CO_2CH_2CH_3$, —$CONH_2$ or —$CONHCH_3$.

7. A compound according to claim 1 wherein the N-linked imidazolyl group is further substituted by a group selected from $C_{3-5}$ cycloalkyl or $C_{3-5}$cycloalkyl$C_{1-2}$alkyl, and preferably a cyclopropyl, cyclobutyl or cyclopropylmethyl group.

8. A compound according to claim I wherein the group Het—$CH_2$— is attached at the 5- or 6-position on the benzofuran ring, preferably the 5-position on the benzofuran ring.

9. A compound according to claim 1 wherein $R^1$ represents a hydrogen atom or a halogen atom or a group selected from $C_{1-6}$alkyl, $C_{1-6}$alkoxy or fluoro$C_{1-6}$alkyl, preferably a hydrogen atom or a halogen atom or a $C_{1-3}$ alkyl group, more preferably a halogen atom, most preferably a bromine atom.

10. A compound according to claim 1 wherein $R^3$ represents the group —$CONHSO_2R^{17}$ wherein $R^{17}$ preferably represents a phenyl group; or $R^3$ represents the group

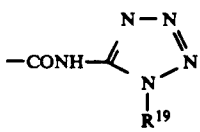

wherein R$^{19}$ preferably represents a hydrogen atom.

11. A compound according to claim 1 wherein R$^4$ and R$^5$ each independently represents a hydrogen atom or a halogen atom, preferably R$^4$ and R$^5$ each independently represents a hydrogen atom.

12. A compound of formula (I)

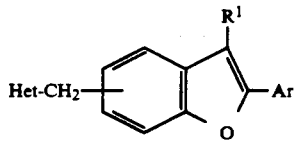

or a physiologically acceptable salt, solvate or metabolically labile ester thereof wherein
R$^1$ represents a halogen atom;
Ar represents the group

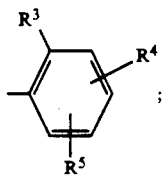

R$^3$ represents a group selected from —CONH-SO$_2$R$^{17}$ or

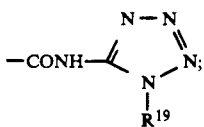

R$^4$ and R$^5$ each independently represent a hydrogen atom;
Het represents an N-linked imidazolyl group optionally substituted at the 2-positioned by a C$_{1-6}$alkyl group, the imidazolyl group being substituted at the 4- and 5-positioned by two further substituents selected from a halogen atom or a group selected from C$_{3-7}$cycloalkyl or —(CH$_2$)$_n$COR$^7$;
R$^7$ represents a group selected from hydroxy, C$_{1-6}$alkoxy or the group —NR$^{10}$R$^{11}$;
R$^{10}$ and R$^{11}$ each independently represent a hydrogen atom;
R$^{17}$ represents a phenyl group;
R$^{19}$ represents a hydrogen atom; and
n represents an integer from 0 to 4, preferably 0, 1 or 2, especially 0 or 1.

13. A compound selected from
1-[[3-bromo-2-[2-[[(phenylsulphonyl)amino]carbonyl)phenyl]-5-benzofuranyl)methyl]-2-ethyl-4-methyl-1H-imidazole-5-carboxamide;
1-[[3-bromo-2-[2-[[(phenylsulphonyl)amino]carbonyl]phenyl]-5-benzofuranyl]methyl]-2-ethyl-N,4-dimethyl-1H-imidazole-5-carboxamide;
1-[[3-bromo-2-[2-[[(phenylsulphonyl)amino]carbonyl]phenyl]-5-benzofuranyl]methyl]-N,2-diethyl-4-methyl-1H-imidazole-5-carboxamide;
1-[[3-bromo-2-[2-[[(phenylsulphonyl)amino]carbonyl]phenyl]-5-benzofuranyl]methyl]-4-chloro-2-ethyl-1H-imidazole-5-carboxamide;
1-[[3-bromo-2-(2-[[(phenylsulphonyl)amino]carbonyl]phenyl]-5-benzofuranyl]methyl]-4-chloro-2-ethyl-N-methyl-1H-imidazole-5-carboxamide;
1-[[3-bromo-2-[2-[[(phenylsulphonyl)amino]carbonyl]phenyl]-5-benzofuranyl)methyl]-4-chloro-N,2-diethyl-1H-imidazole-5-carboxamide;
1-[[3-bromo-2-[2-[[(phenylsulphonyl)amino]carbonyl]phenyl]-5-benzofuranyl]methyl]-4-methyl-2-propyl-1H-imidazole-5-carboxamide;
1-[[3-bromo-2-[2-[[(phenylsulphonyl)amino]carbonyl]phenyl]-5-benzofuranyl]methyl]-N,4-dimethyl-2-propyl-1H-imidazole-5-carboxamide;
1-[[3-bromo-2-[2-[[(phenylsulphonyl)amino]carbonyl]phenyl]-5-benzofuranyl]methyl]-N-ethyl-4-methyl-2-propyl-1H-imidazole-5-carboxamide;
1-[[3-bromo-2-[2-[[(phenylsulphonyl)amino]carbonyl]phenyl]-5-benzofuranyl9 methyl]-4-chloro-2-propyl-1H-imidazole-5-carboxamide;
1-[[3-bromo-2-[2-[[(phenylsulphonyl)amino]carbonyl]phenyl]-5-benzofuranyl]methyl]-4-chloro-N-methyl-2-propyl-1H-imidazole-5-carboxamide;
1-[[3-bromo-2-[2-[[(phenylsulphonyl)amino]carbonyl]phenyl]-5-benzofuranyl]methyl]-4-chloro-N-ethyl-2-propyl-1H-imidazole-5-carboxamide;
1-[[3-bromo-2-[2-[[(1H-tetrazol-5-yl)amino]carbonyl]phenyl]-5-benzofuranyl]methyl]-2-ethyl-4-methyl-1H-imidazole-5-carboxamide;
1-[[3-bromo-2-[2-[[(1H-tetrazol-5-yl)amino]carbonyl]phenyl]-5-benzofuranyl]methyl]-2-ethyl-N,4-dimethyl-1H-imidazole-5-carboxamide;
1-[[3-bromo-2-[2-[[(1H-tetrazol-5-yl)amino]carbonyl]phenyl]-5-benzofuranyl]methyl]-N,2-diethyl-4-methyl-1H-imidazole-5-carboxamide;
1-[[3-bromo-2-[2-[[(1H-tetrazol-5-yl)amino]carbonyl]phenyl]-5-benzofuranyl]methyl]-4-chloro-2-ethyl-1H-imidazole-5-carboxamide;
1-[[3-bromo-2-[2-[[(1H-tetrazol-5-yl)amino]carbonyl]phenyl]-5-benzofuranyl]methyl]-4-chloro-2-ethyl-N-methyl-1H-imidazole-5-carboxamide;
1-[[3-bromo-2-[2-[[(1H-tetrazol-5-yl)amino]carbonyl]phenyl]-5-benzofuranyl]methyl]-4-chloro-N,2-diethyl-1H-imidazole-5-carboxamide;
1-[[3-bromo-2-[2-[[(1H-tetrazol-5-yl)amino]carbonyl]phenyl]-5-benzofuranyl]methyl]-4-methyl-2-propyl-1H-imidazole-5-carboxamide;
1-[[3-bromo-2-[2-[[(1H-tetrazol-5-yl)amino]carbonyl]phenyl]-5-benzofuranyl]methyl]-N,4-dimethyl-2-propyl-1H-imidazole-5-carboxamide;
1-[[3-bromo-2-[2-[[(1H-tetrazol-5-yl)amino]carbonyl]phenyl]-5-benzofuranyl]methyl]-N-ethyl-4-methyl-2-propyl-1H-imidazole-5-carboxamide;
1-[[3-bromo-2-[2-[[(1H-tetrazol-5-yl)amino]carbonyl]phenyl]-5-benzofuranyl]methyl]-4-chloro-2-propyl-1H-imidazole-5-carboxamide;
1-[[3-bromo-2-[2-[[(1H-tetrazol-5-yl)amino]carbonyl]phenyl]-5-benzofuranyl]methyl)-4-chloro-N-methyl-2-propyl-1H-imidazole-5-carboxamide;
1-[[3-bromo-2-[2-[[(1H-tetrazol-5-yl)amino]carbonyl]phenyl]-5-benzofuranyl]methyl]-4-chloro-N-ethyl-2-propyl-1H-imidazole-5-carboxamide;
or a physiologically acceptable salt, solvate or metabolically labile ester thereof.

14. A compound selected from

1-[[3-bromo-2-[2-[[(phenylsulphonyl)amino]carbonyl]phenyl]-5-benzofuranyl]methyl]-4-cyclopropyl-2-ethyl-1H-imidazole-5-carboxylic acid;

1-[[3-bromo-2-(2-[[(phenylsulphonyl)amino)carbonyl]phenyl]-5-benzofuranyl]methyl]-4-cyclopropyl-2-propyl-1H-imidazole-5-carboxylic acid;

1-[[3-bromo-2-[2-[[(phenylsulphonyl)amino]carbonyl]phenyl]-5-benzofuranyl]methyl]-4-cyclopropyl-2-ethyl-1H-imidazole-5-carboxamide;

1-[[3-bromo-2-[2-[[(phenylsulphonyl)amino]carbonyl]phenyl]-5-benzofuranyl]methyl]-4-cyclopropyl-2-propyl-1H-imidazole-5-carboxamide;

1-[[3-bromo-2-[2-[[phenylsulphonyl)amino]carbonyl]phenyl]-5-benzofuranyl]methyl]-4-cyclopropyl-2-ethyl-N-methyl-1H-imidazole-5-carboxamide;

1-[[3-bromo-2-[2-[[(phenylsulphonyl)amino]carbonyl]phenyl]-5-benzofuranyl]methyl]-4-cyclopropyl-N-methyl-2-propyl-1H-imidazole-5-carboxamide;

1-[[3-bromo-2-[2-[[(phenylsulphonyl)amino]carbonyl]phenyl]-5-benzofuranyl]methyl]-4-cyclopropyl-N,2-diethyl-1H-imidazole-5-carboxamide;

1-[[3-bromo-2-[2-[[phenylsulphonyl)amino]carbonyl]phenyl]-5-benzofuranyl]methyl]-4-cyclopropyl-N-ethyl-2-propyl-1H-imidazole-5-carboxamide;

or a physiologically acceptable salt, solvate or metabolically labile ester thereof.

15. A pharmaceutical composition comprising at least one compound of formula (I) as defined in claim 1 or a physiologically acceptable salt, solvate or metabolically labile ester thereof, together with at least one physiologically acceptable carrier or excipient.

16. 1-[[3-bromo-2-[[[(1H-tetrazol-5-yl)amino]carbonyl]phenyl]-5-benzofuranyl]methyl]-2-butyl-4-chloro-1H-imidazole-5-carboxylic acid or physiologically acceptable salt, solvate or metabolically labile ester thereof.

* * * * *